US00PP27878P2

(12) United States Plant Patent
Hansen et al.

(10) Patent No.: US PP27,878 P2
(45) Date of Patent: Apr. 11, 2017

(54) ***BUDDLEIA* PLANT NAMED 'CROWN JEWELS'**

(50) Latin Name: ***Buddleia davidii* (L.)**
Varietal Denomination: Crown Jewels

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 149 days.

(21) Appl. No.: 14/545,728

(22) Filed: Jun. 10, 2015

(51) Int. Cl.
*A01H 5/00* (2006.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell |
| PP17,332 | P2 | 1/2007 | Moore |
| PP19,934 | P2 | 4/2009 | Davis |
| PP19,935 | P2 | 4/2009 | Bloom |
| PP19,950 | P3 | 4/2009 | Werner |
| PP19,991 | P3 | 5/2009 | Werner |
| PP22,063 | P2 | 8/2011 | Valin |
| PP22,064 | P2 | 8/2011 | Valin |
| PP22,065 | P2 | 8/2011 | Podaras |
| PP22,066 | P2 | 8/2011 | Podaras |
| PP22,067 | P2 | 8/2011 | Podaras |
| PP22,068 | P2 | 8/2011 | Podaras |
| PP22,069 | P2 | 8/2011 | Podaras |
| PP22,080 | P2 | 8/2011 | Podaras |
| PP22,081 | P2 | 8/2011 | Podaras |
| PP22,098 | P2 | 8/2011 | Podaras |
| PP22,108 | P2 | 9/2011 | Podaras |
| PP22,109 | P2 | 9/2011 | Podaras |
| PP22,110 | P2 | 9/2011 | Podaras |
| PP22,142 | P2 | 9/2011 | Podaras |
| PP22,143 | P2 | 9/2011 | Podaras |
| PP22,144 | P2 | 9/2011 | Podaras |
| PP22,177 | P2 | 10/2011 | Podaras |
| PP22,367 | P2 | 12/2011 | Podaras |
| PP22,465 | P2 | 1/2012 | Brand |
| PP22,680 | P2 | 4/2012 | Senior |
| PP23,214 | P2 | 11/2012 | Moore |
| PP23,425 | P2 | 2/2013 | Werner et al. |
| PP23,461 | P2 | 3/2013 | Valin |
| PP23,462 | P2 | 3/2013 | Valin |
| PP23,463 | P2 | 3/2013 | Valin |
| PP23,464 | P2 | 3/2013 | Valin |
| PP23,498 | P2 | 3/2013 | Podaras |
| PP24,015 | P3 | 11/2013 | Werner |
| PP24,016 | P3 | 11/2013 | Werner |
| PP24,030 | P3 | 11/2013 | Podaras |

*Primary Examiner* — Susan McCormick Ewoldt
*Assistant Examiner* — Karen Redden

(57) ABSTRACT

*Buddleia* 'Crown Jewels' is a short, mounded, multi-stemmed, winter-hardy butterfly bush with long, compact, flowering thyrse over a long season beginning mid-summer with sweetly-fragrant red-purple flowers that are attractively offset by chartreuse to bright yellow foliage.

1 Drawing Sheet

Botanical classification: *Buddleia davidii* (L.).
Variety denomination: 'Crown Jewels'.

BACKGROUND AND ORIGIN OF THE PLANT

The present invention relates to the new and distinct winter-hardy butterfly bush plant, *Buddleia* 'Crown Jewels' from a single seedling among thousands of seeds collected in the fall of 2010 from the breeding program of the inventors Hans A. Hansen and Kevin A. Hurd at a nursery in Zeeland, Mich., USA. The new plant, originally assigned the breeder code #HK10-17-300, is from an open pollinated cross between a proprietary hybrid #HK9-21-02 (not patented) as the female or seed parent and an unknown male or pollen parent. The female parent was planted in amongst several hundred other hybrids, so the potential for recombination was great.

*Buddleia* 'Crown Jewels' was first asexually propagated in 2012 by stem cuttings at the same nursery in Zeeland, Mich. The resultant asexually propagated plants have been found to be stable and true to type in successive generations of asexual reproduction.

*Buddleia* 'Crown Jewels' has not been made publically available nor sold more than one year prior to the filing of this application.

BRIEF SUMMARY OF THE PLANT

*Buddleia* 'Crown Jewels' differs from its parents as well as all other winter-hardy butterfly bush plants known to the applicant in many traits. The foliage color of 'Crown Jewels' is chartreuse to bright yellow. The foliage size of 'Crown Jewels' is variable, depending on the position on the stem. Largest leaves are lower on the stem and decrease in size distally. Compared to the proprietary female parent, HK9-21-02, 'Crown Jewels' is more compact in habit.

The nearest comparison plants include: *Buddleia* 'Evil Ways' (not patented) with short spikes of dark purple flowers, *Buddleia* 'Santana' U.S. Plant Pat. No. 12,383 with gold margins and green centers, *Buddleia* 'Harlequin' (not patented) with light green leaf centers and creamy margins, *Buddleia* 'Summer Skies' U.S. Plant Pat. No. 22,465 and *Buddleia* 'White Profusion' (not patented).

The following Table 1 further demonstrates some comparisons with the new plant and the nearest comparison cultivars.

TABLE 1

| CULTIVAR | LEAF COLOR | FLOWER COLOR | HABIT | SIZE (H × W) |
|---|---|---|---|---|
| 'Crown Jewels' | yellow to chartreuse | red-purple | mounded | 120 cm × 120 cm |
| 'Harlequin' | light green with cream margin | red-purple | towering | 180 cm × 165 cm |
| 'Santana' | green with yellow margin | purple-red | upright | 170 cm × 150 cm |
| 'Summer Skies' | light green with cream margin | lavender | sprawling | 150 cm × 165 cm |
| 'White Profusion' | green | white | upright | 180 cm × 150 cm |

*Buddleia* 'Crown Jewels' is a unique winter-hardy butterfly bush different from all other *Buddleia* cultivars known to the inventor based on the following combined traits:

1. Winter-hardy shrub, with multiple-stemmed, branched, short, mounded habit.
2. Many-flowered compact thyrse over a prolonged season beginning mid-summer.
3. Flowers of red-purple petals.
4. Lanceolate foliage of chartreuse to bright yellow.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
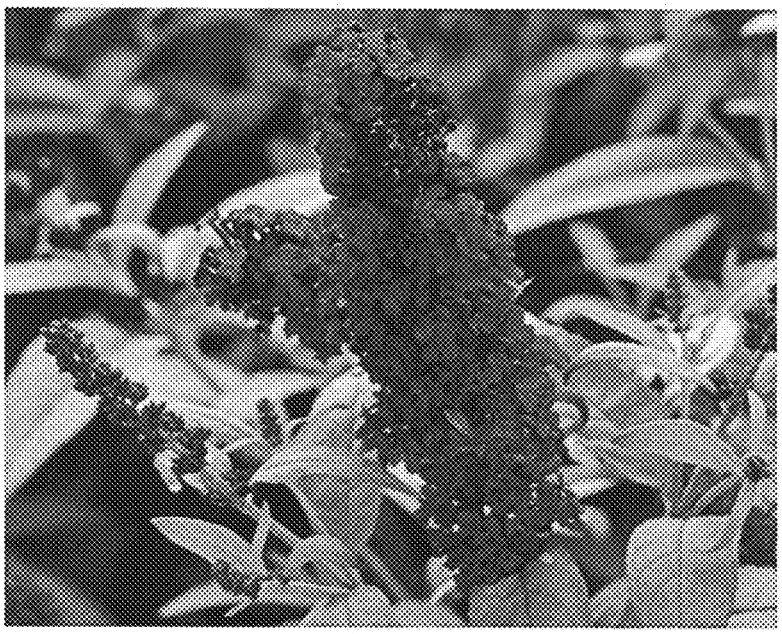
FIG. 1 shows a close-up of the flowers.
Figure 2:
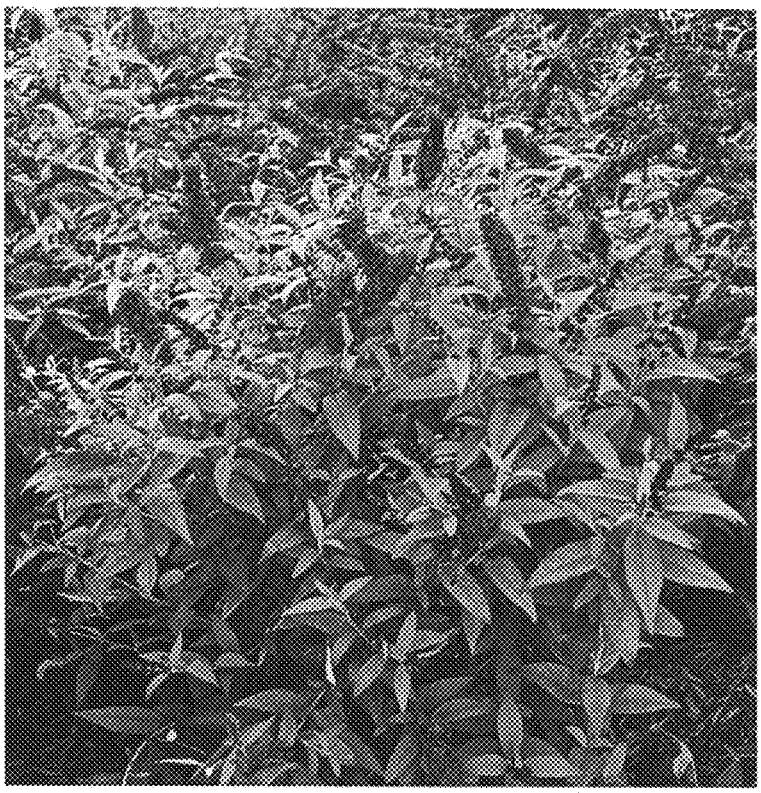
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Crown Jewels', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand open-sun field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Proprietary hybrid #HK9-21-02 (not patented) as the female or pod parent times an unknown open-pollination as the male or pollen parent.

Propagation:

*Method*.—Softwood cuttings.

*Time to initiate roots*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type; becoming woody to 1.5 cm diameter.

*Crop time*.—Under normal summer growing conditions 12 to 16 weeks to flower in a four-liter container from cutting. Plant vigor is very good.

Plant description:

*Plant shape and habit*.—Winter-hardy, herbaceous, semi-woody, well-branched perennial shrub with about 10 thick upright and branched main stems producing an upright mound about 120 cm tall and about 120 cm wide; width of plant about 120 cm.

*Stem*.—Rounded and woody in lower portion rounded in cross section with exfoliating bark; younger upper portion puberulent and quadrangular in cross section; strong and flexible; average about 80 cm tall from soil line to just below terminal flowers, and about 1.0 cm diameter at the base; before distal flowers about 12 branches per main stem below terminal flower thyrse, extending at about 55° to 60° angle from horizontal; longest branches about 45 cm long, decreasing distally.

*Stem color*.—Just below flowers between RHS 145D and RHS 155C with slight tinting of nearest RHS 184A especially on ridges, and striated in about basal 10 cm with fissures of nearest RHS 165D and between RHS 165A and RHS 165B.

*Plant size*.—Unpinched plant with stems flowering to about 120 cm tall; overall plant about 120.0 cm wide.

*Internode*.—About 15 nodes per stem, average internode length about 5.3 cm on unpinched plant; upper nodes more pubescent than lower nodes.

*Node color*.—Same color as surrounding stem to slightly more tinted with RHS 184A.

Foliage description: Opposite, decussate; serrulate; puberulent abaxial and glabrous adaxial; elliptic to lanceolate with attenuate base and acute apex; no foliar fragrance detected.

*Leaf blade size*.—Up to about 15.2 cm long and about 4.4 cm wide, average about 14 cm long and about 3.0 cm wide; becoming smaller in distal portion of stem.

*Foliage color*.—Young expanding leaf adaxial side nearest RHS 153C and abaxial nearest RHS 192C; mature leaves adaxial side variable with some portions nearest RHS 2B and other regions of the same leaf between RHS 139A and RHS 139B and abaxial between RHS 11D and lighter than RHS 149D.

*Veins*.—Reticulate; abaxial raised, adaxial slightly impressed.

*Vein color*.—Young expanding adaxial nearest RHS N144D, abaxial nearest RHS 155B; mature adaxial variable between RHS 145A and RHS 2B, abaxial between RHS 145D and RHS 155C.

*Petioles*.—Glaucous and glabrous adaxial, pubescent abaxial; flatted partially top to bottom; average size about 1.0 cm long and about 2.0 mm wide at the point of attachment to stem.

*Petiole color*.—Adaxial margins nearest RHS 139B and center vein between RHS 192C and RHS 145C, abaxial nearest RHS 145D.

Inflorescence description: Glomerate thyrse consisting of about 400 self-cleaning salverform flowers; to about 27.5 cm long and 4.0 cm wide, beginning in mid-July and continuing until late October in Michigan.

*Buds*.—Narrowly spatulate, apex rounded; one day prior to opening about 11.0 mm long and about 3.5 mm in diameter in club, tube portion about 1.0 mm diameter and about 8.0 mm long.

*Bud color*.—Nearest RHS N81A in both tube and unopened blade portion; buds about three days from opening nearest RHS 72B in tube and unopened blade portion nearest RHS N81A.

*Sepals*.—Typically four, proximal two-thirds connate adpressed to corolla tube; acute apex; glabrous adaxial and pubescent abaxial; margin entire, edentate; fused in about the basal 1.5 mm and split in about the terminal 1.0 mm; forming a corolla about 2.5 mm long and about 2.0 mm across; individually less than about 1.0 mm wide at point of fusion.

*Sepal color*.—Adaxial nearest RHS 193D, abaxial between RHS 193C and RHS 193D.

*Flowers fragrance*.—Pleasantly and distinctly sweet.

*Petals*.—Four, rarely five; glabrous; fused into salver-form with, typically straight cylindrical tube about 9.0 mm long and 2.0 mm diameter, and a flattened face about 10.0 mm across; petal blade rounded with crenate margin; blade to about 4.5 mm across and about 4.0 mm long from fused face; center flattened face portion of blade fused about 2.0 mm.

*Petal color*.—Adaxial center between RHS 28A and RHS N25A in the tube surrounded by a thin irregular band of less than 0.5 mm width of between RHS 18A and RHS 18B, adaxial face blades nearest RHS N81B; abaxial tube nearest RHS 64A and abaxial petal blades nearest RHS N81B.

*Gynoecium*.—Pistil: one; about 3.0 mm long. Style: short, round, glabrous; about 2.0 mm long and less than 0.2 mm diameter; color nearest RHS 144C. Stigma: oblong, minutely puberulent; about 1.0 mm, in diameter and less than 0.7 mm long; color nearest RHS 141B. Ovary: superior; globose; about 1.0 mm across at base and 1.0 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and 0.5 mm wide; color nearest RHS 4D. Pollen: numerous, globose, less than 0.1mm long; color nearest RHS 4D.

*Pedicel*.—Short, puberulent; about 2.0 mm long and about 0.5 mm diameter; color nearest RHS 152B.

*Peduncle*.—Quadrangular, pubescent, flexible and strong; to about 27.5 cm long.

*Peduncle color*.—Between RHS 148D and RHS 138B.

*Fruit*.—Moderate fruit set; oblong with acute apex; glabrous, bi-valved, septicidal capsule; about 8.0 mm long and about 2.0 mm diameter.

*Fruit color*.—As maturing nearest RHS 183C; when mature and dehiscing between RHS 173B and RHS 173C.

*Seed*.—Elongated ellipse with sharply acute ends; less than about 2.0 mm long and about 0.1 mm diameter in center.

*Seed color*.—Nearest RHS 200A.

Disease resistance: Resistance to deer browsing has been observed. Further resistance beyond that of other known winter-hardy butterfly bush cultivars has not been noted. The plant grows best with plenty of moisture and adequate drainage, but is able to tolerate some drought when mature.

Hardiness: At least from USDA zone 6 through 10.

We claim:

1. A new cultivar of winter-hardy butterfly bush *Buddleia* plant named 'Crown Jewels' as herein illustrated and described, suitable for potted plant culture, landscaping as a specimen or en masse or as cut flower purposes.

* * * * *